United States Patent
Phillip et al.

(10) Patent No.: US 9,056,804 B2
(45) Date of Patent: Jun. 16, 2015

(54) UREASE INHIBITOR FORMULATIONS

(71) Applicant: Incitec Pivot Limited, Victoria (AU)

(72) Inventors: Arpad T. Phillip, Victoria (AU); Roydon Hildebrand, Queensland (AU); Rohan Davies, Victoria (AU); Charlie Walker, Victoria (AU)

(73) Assignee: Incitec Pivot Limited, Victoria (AU)

( * ) Notice: Subject to any disclaimer, the term of this patent is extended or adjusted under 35 U.S.C. 154(b) by 0 days.

(21) Appl. No.: 14/357,712

(22) PCT Filed: Nov. 13, 2012

(86) PCT No.: PCT/AU2012/001395
§ 371 (c)(1),
(2) Date: May 12, 2014

(87) PCT Pub. No.: WO2013/071344
PCT Pub. Date: May 23, 2013

(65) Prior Publication Data
US 2014/0326030 A1  Nov. 6, 2014

(30) Foreign Application Priority Data

Nov. 14, 2011  (AU) ................. 2011904729

(51) Int. Cl.
| | |
|---|---|
| C05C 9/00 | (2006.01) |
| C07C 273/14 | (2006.01) |
| C09K 17/00 | (2006.01) |
| C05G 3/08 | (2006.01) |
| C07F 9/22 | (2006.01) |
| A01N 57/28 | (2006.01) |
| A01N 57/30 | (2006.01) |
| C09K 15/28 | (2006.01) |

(52) U.S. Cl.
CPC ............. *C05G 3/08* (2013.01); *C07C 273/14* (2013.01); *C07F 9/224* (2013.01); *A01N 57/28* (2013.01); *A01N 57/30* (2013.01); *C09K 15/28* (2013.01)

(58) Field of Classification Search
None
See application file for complete search history.

(56) References Cited

U.S. PATENT DOCUMENTS

| | | | |
|---|---|---|---|
| 2009/0227458 A1* | 9/2009 | Boucher et al. ............... | 504/244 |
| 2010/0206031 A1 | 8/2010 | Whitehurst et al. | |
| 2011/0154874 A1 | 6/2011 | Rahn et al. | |
| 2013/0157850 A1* | 6/2013 | Wilson et al. ................. | 504/101 |

FOREIGN PATENT DOCUMENTS

| | | |
|---|---|---|
| GB | 1094802 | * 12/1967 |
| GB | 1371694 A | 10/1974 |
| WO | 97/22568 A1 | 6/1997 |
| WO | 2009/079994 A2 | 7/2009 |
| WO | 2010/072184 A2 | 7/2010 |

OTHER PUBLICATIONS

International Search Report, PCT Application No. PCT/AU2012/001395, mailed Dec. 17, 2012.

* cited by examiner

*Primary Examiner* — Wayne Langel
(74) *Attorney, Agent, or Firm* — Kilpatrick Townsend & Stockton LLP

(57) ABSTRACT

There is provided a liquid urease inhibitor formulation comprising an urease inhibitor and a primary solvent selected from the group consisting of dialkyl sulfones, polymethylene cyclic sulfones, and mixtures thereof. A method for inhibiting urease hydrolysis of urea containing fertilizer or waste using said liquid urease inhibitor formulation is also described.

23 Claims, No Drawings

UREASE INHIBITOR FORMULATIONS

The present application is a National Phase application of International Application No. PCT/AU2012/001395 filed Nov. 13, 2012, which claims priority to Australian Patent Application No. 2011904729 filed on Nov. 14, 2011, the contents of which are incorporated herein by reference.

FIELD OF THE INVENTION

The invention relates to formulations comprising urease inhibitors. In particular, the invention relates to formulations comprising urease inhibitors for application to urea-based fertilisers and waste containing urea compounds to inhibit the effect of urease activity on such fertilisers and wastes.

BACKGROUND OF THE INVENTION

In this specification, where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Nitrogen is an important plant nutrient. Urea ($CO(NH_2)_2$) represents more than 40% of the total nitrogen fertiliser applied to agricultural crops worldwide. However, urea is readily degraded in soil by the "urease" group of enzymes, which catalyses the reaction of urea with water to produce gaseous ammonia and ammonium ions (referred to as "urea hydrolysis"). The ammonia is readily volatile from the treated soil; leading to a loss of up to 60% of the applied urea as a result of this enzymatic hydrolysis.

In order to delay this hydrolysis, "urease inhibitors" have been applied to urea based fertilisers in an attempt to reduce the rate of urea hydrolysis and subsequent loss of ammonia. Examples of such urease inhibitors include the N-alkyl thiophosphoric triamides such as N-(n-butyl)thiophosphoric triamide (NBPT). However, NBPT is a waxy, sticky, heat-sensitive and water-sensitive material and so particular formulations are required to minimise decomposition during storage and distribution. Examples of such formulations include:
  a concentrated solution of an N-alkyl thiophosphoric triamide in a solvent mixture of glycols (eg propylene glycol) and liquid amides (eg N-methylpyrrolidone) (see for example international patent application no WO 97/22568);
  a mixture comprising a thiophosphoric acid triamide and a compound containing an amino group having a boiling point of more than 100° C. (see for example international patent application no WO 2009/079994); and
  a liquid composition containing a phosphoric or thiophosphoric triamide derivative and one or more of esters of hydroxyacids, heterocyclic alcohols, cyclic esters of carbonic acid and esters of dicarboxylic acids (see for example international patent application no WO 2010/072184).

The existing urease inhibitors formulations currently used in agriculture (e.g. the commercial product called Agrotain™ (trade mark of Phosphate Resource Partners Limited Partnership, registered in some countries)) suffer from a number of disadvantages in use, including:
  limited storage stability of the treated urea;
  health and safety concerns regarding the solvents used in the formulation; and
  ecotoxicology concerns regarding the effect of solvents used in the formulation once in the aquatic and terrestrial environment.

Therefore, there is a need for an improved urease inhibitor formulation which addresses at least one of these disadvantages.

SUMMARY OF THE INVENTION

It has been discovered that new solvent combinations and/or mixtures of active ingredients address at least one of the above disadvantages. The new formulations continue to enhance the efficiency of urea-based fertilisers by delaying urea hydrolysis in soils and reducing liberation of ammonia into the atmosphere.

According to a first aspect of the invention, there is provided a liquid urease inhibitor formulation comprising:
  (a) a urease inhibitor selected from the group consisting of N-substituted thiophosphoric triamides and N-substituted phosphoric triamides represented by Structure I and mixtures thereof,

Structure I wherein X=O or S, $R^1$=unsubstituted and substituted $C_3$-$C_6$ alkyl, unsubstituted and substituted $C_5$-$C_8$ cyclo alkyl, phenyl and substituted phenyl having a nitro, amino, alkyl, or halide substituent; and Y=H, $NO_2$, halide, $NH_2$ or $C_1$ to $C_8$ alkyl; and (b) a primary solvent selected from the group consisting of dialkyl sulfones according to Structure II, polymethylene cyclic sulfones according to Structure III, and mixtures thereof;

Structure II wherein $R^2$ = alkyl $C_1$ to $C_6$
$R^3$ = alkyl $C_1$ to $C_6$

Structure III wherein $n$ = 3 to 6 wherein the urease inhibitor is soluble in the primary solvent.

The urease inhibitors used in the formulations according to the invention include:
  N-alkyl-thiophosphoric triamides;
  N-alkyl-phosphoric triamides;
  N-cycloalkyl-thiophosphoric triamides;
  N-cycloalkyl-phosphoric triamides;
  N-aryl-thiophosphoric triamides; or
  N-aryl-phosphoric triamides, where the alkyl, cycloalkyl or aryl groups may be further substituted with chloro-, nitro- or amino-groups. Commonly available urease inhibitors include N-butyl thiophosphoric triamide (NBPT), N-cyclohexyl phosphoric triamide (CHPT) and 2-nitrophenyl phosphoric triamide (2-NPT). Many other urease inhibitors can be used in formulations according to the invention as known to those skilled in the art. Combinations of two or more urease inhibitors can also be used in formulations according to the invention. Preferably, the urease inhibitor is present in the formulation in an amount in the range from 0.5 to 51% by weight of the total formulation, more preferably 10 to 20%.

The primary solvents, selected from the specified sulfones, provide excellent stability and solubility for the urease inhibitors. They also have environmental and occupational health and safety advantages. Preferably, the primary solvent is tetramethylene sulfone which is readily biodegradable in soils (half life is 10 days) and does not present an ecotoxicological hazard (the LC50 is greater than 1000 mg/l for fish, algae and invertebrates). Tetramethylene sulfone has a high boiling point (284° C.), is non-flammable and is not classified as a Dangerous Good or Hazardous Substance.

The use of the primary solvents in formulations according to the invention have beneficial properties not achieved by the prior art solvent systems, including:
- the urease inhibitors are stable in the concentrated solution even at elevated temperatures (up to 40° C.) for more than 12 months;
- the formulations according to the invention can be applied directly into liquid fertilizer or liquid waste containing urea compounds;
- the formulations according to the invention can be sprayed directly onto, and mixed into, solid wastes containing urea compounds;
- the formulations according to the invention have low viscosity, thereby facilitating rapid and uniform spreading on the surface of urea granules;
- the formulations according to the invention can be applied to the surface of urea granules, which absorb the formulation, penetrating deep into the solid granule ("impregnating" the granule structure);
- urea granules coated with the formulations according to the invention remain robust during storage, transport and handling, thereby retaining their hardness and crush strength;
- urea granules coated with the formulations according to the invention hydrolyse more slowly in soils than urea granules treated with the prior art formulation, thereby achieving the desired slow release of ammonia for most efficient uptake by crops and plants. The slower rate of urea hydrolysis leads to a lower pH in proximity to the urea granules which results in a higher ratio of stable ammonium to ammonia; and
- urea granules coated with the formulations according to the invention remain stable and retain their urease inhibition activity during storage in hot climates up to 40° C. for more than 3 months.

The formulations according to the invention give superior performance with unexpected results not previously obtained with other solvent systems.

Preferably, the primary solvent is present in the formulation in an amount in the range from 10 to 80% by weight of the total formulation, more preferably 40 to 70%.

In a preferred embodiment, the liquid urease inhibitor formulation further comprises:

(c) a buffering agent and stabiliser selected from the group consisting of hydroxyethyl and hydroxypropyl amines according to Structure IV, in which the amine can be a primary, secondary or tertiary amine and the number of hydroxyethyl or hydroxypropyl groups can be 1, 2 or 3,

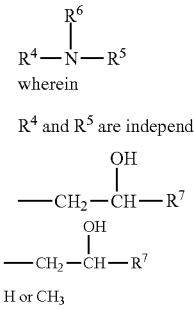

Structure IV wherein $R^4$ and $R^5$ are independently H, $C_1$-$C_6$ alkyl or $-CH_2-CH(OH)-R^7$ $R^6 = -CH_2-CH(OH)-R^7$ $R^7$ = H or $CH_3$ The buffering agents and stabilisers further improve the storage stability of the urease inhibitors in the formulations according to the invention. Preferred buffering agents and stabilisers are triethanolamine, monoethanolamine and mixtures thereof. Preferably, the buffering agents and stabilisers are present in the formulation in an amount in the range from 1 to 50% by weight of the total formulation, more preferably 20 to 50%.

In a preferred embodiment, the liquid urease inhibitor formulation further comprises:

(d) a non-ionic surfactant having wetting agent properties selected from the group consisting of aliphatic alcohol alkoxylates, alkylphenol alkoxylates and mixtures thereof.

The non-ionic surfactant improves the wetting and spreading effect of formulations according to the invention on the surface of the urea granules. An example of a suitable non-ionic surfactant are the products available under the Terwet™ brand. Preferably, the nonionic surfactant is present in the formulation in an amount in the range from 0.1 to 2.0% by weight of the total formulation The formulations according to the invention may further comprise additional components such as amides, esters, heterocyclic alcohols and glycols.

EXAMPLES

Various embodiments/aspects of the invention will now be described with reference to the following non-limiting examples.

Example 1

A formulation was prepared according to the invention.

| Components | Amount (grams) |
|---|---|
| Sulfolane (tetramethylene sulfone) | 690 |
| Triethanolamine | 100 |
| N-butyl thiophosphoric triamide | 200 |
| Terwet 245 (surfactant) | 10 |
| Total Mass | 1000 |

The components were mixed in the order shown and stirred at 50° C. for 30 minutes. A clear solution, with no insoluble solids, was obtained.

Example 2

A formulation was prepared according to the invention.

| Components | Amount (grams) |
| --- | --- |
| Sulfolane | 690 |
| Monoethanolamine | 100 |
| N-butyl thiophosphoric triamide | 200 |
| Terwet 245 | 10 |
| Total Mass | 1000 |

The above formulation was prepared according to the method described in Example 1.

Example 3

A formulation was prepared according to the invention.

| Components | Amount grams |
| --- | --- |
| Sulfolane | 400 |
| Triethanolamine | 390 |
| N-butyl thiophosphoric triamide | 200 |
| Terwet 245 | 10 |
| Total Mass | 1000 |

The above formulation was prepared according to the method described in Example 1.

Example 4

A formulation was prepared according to the invention.

| Components | Amount (grams) |
| --- | --- |
| Sulfolane | 440 |
| Triethanolamine | 440 |
| N-butyl thiophosphoric triamide | 100 |
| 2-nitrophenyl phosphoric triamide | 10 |
| Terwet 245 | 10 |
| Total Mass | 1000 |

The above formulation was prepared according to the method described in Example 1.

Example 5

A formulation was prepared according to the invention.

| Components | Amount (grams) |
| --- | --- |
| Sulfolane | 500 |
| Monoethanolamine | 290 |
| N-butyl thiophosphoric triamide | 200 |
| Terwet 245 | 10 |
| Total Mass | 1000 |

The above formulation was prepared according to the method described in Example 1.

Example 6

A formulation was prepared according to the invention.

| Components | Amount (grams) |
| --- | --- |
| Sulfolane | 300 |
| Triethanolamine | 640 |
| N-Cyclohexyl phosphoric triamide | 50 |
| Terwet 245 | 10 |
| Total Mass | 1000 |

The above formulation was prepared according to the method described in Example 1.

Example 7

A formulation was prepared according to the invention.

| Components | Amount (grams) |
| --- | --- |
| Sulfolane | 390 |
| Triethanolamine | 400 |
| N-Butyl thiophosphoric triamide | 200 |
| Terwet 245 | 10 |
| Total Mass | 1000 |

The above formulation was prepared according to the method described in Example 1.

Example 8

A formulation was prepared according to the invention.

| Components | Amount (grams) |
| --- | --- |
| Sulfolane | 470 |
| Triethanolamine | 470 |
| 2-Nitrophenyl phosphoric triamide | 50 |
| Terwet 245 | 10 |
| Total Mass | 1000 |

The above formulation was prepared according to the method described in Example 1.

Example 9

This example investigated the amount of ammonium produced by urea granules treated with formulations according to the invention.

Methodology

An incubation experiment was performed by storing a soil-water suspension at 21° C. for 14 days. Each day, a small aliquot (0.5 ml) of the supernatant aqueous phase was withdrawn and analysed for ammonium ions using flow injection analysis (FIA). The soil-water suspension consisted of:

| | | |
| --- | --- | --- |
| soil sample, 60% water holding capacity | 40 | grams |
| Water | 200 | grams |
| Urea | 400 | mg |
| N-butyl thiophosphoric triamide | 400 | μg |
| Solvents | 1600 | μg |

The solvents used in this experiment were those used in Examples 5 and 7 above.

The test solutions contained 400 μg NBPT per 200 ml water. The results are shown in Table 2.

TABLE 2

| Test Solution | $NH_4^+$ (mg/l) | % Inhibition | Urea Hydrolysed (mg) |
|---|---|---|---|
| Control (no Inhibitor) | 29.9 | — | 256 |
| Agrotain ™ | 8.2 | 73 | 70 |
| Example 7 | 8.4 | 72 | 72 |
| Example 5 | 8.9 | 70 | 76 |

The control solution of urea, without a urease inhibitor, showed an NH4+ concentration of 29.9 mg/l after 14 days incubation. After converting for a dilution factor (1:20), the quantity of urea hydrolysed in 200 ml of solution was calculated to be 256 mg. This represents a loss of 64% of the original mass of urea added (400 mg) to the aqueous phase.

By contrast, the formulations according to the invention only formed 8.4 and 8.9 mg/l as NH4+. This represents a loss of only 72 and 76 mg urea after 14 days incubation. The % Inhibition was calculated to be 72% and 70% respectively, using the concentrations of NH4+ in the equation:

$$\% \text{ Inhibition} = \frac{(\text{Control} - \text{Test}) * 100}{\text{Control}}$$

By comparison, the standard product "Agrotain™" widely used as a commercial urease inhibitor, gave 73% inhibition in the above experiment.

These results demonstrate that the formulations prepared according to this invention (Examples 5 and 7) are at least equivalent to the standard formulation Agrotain™, prepared according to the prior art.

Example 10

This example investigated the amount of ammonium produced by urea granules treated with formulations according to the invention.

Methodology

An incubation experiment was performed by storing a soil-water suspension at 21° C. for 17 days. The ammonium produced was measured as per Example 9. The results are shown in Table 3. The incubation mixture contained:

| Soil sample | 40 grams |
|---|---|
| Water | 200 grams |
| Urea | 400 mg |
| Solvents | 1600 μg |
| Urease Inhibitor | 50 to 400 μg |

The solvents and urease inhibitor used in this experiment were those used in Examples 5 and 8 above.

TABLE 3

| Test Solution | Urease Inhibitor | Inhibitor amount (μg/200 ml) | % inhibition (17 days) |
|---|---|---|---|
| Control (Urea only) | Nil | Nil | Nil |
| Agrotain ™ | NBPT | 400 | 73 |
| Example 5 | NBPT | 400 | 84 |

TABLE 3-continued

| Test Solution | Urease Inhibitor | Inhibitor amount (μg/200 ml) | % inhibition (17 days) |
|---|---|---|---|
| Example 8 | 2-NPT | 100 | 80 |
| Example 8 | 2-NPT | 50 | 72 |

The above results show that Example 5 appears to perform more effectively than the standard product Agrotain™ (84% and 73% inhibition respectively, after 17 days).

The urease inhibitor 2-NPT (2-nitrophenyl phosphoric triamide) was superior in performance when compared to NBPT. Even at 50 μg/200 ml water, (Example 8) the active 2-NPT gave 72% inhibition, similar to NBPT at 400 μg/200 ml. This indicates that 2-NPT is about eight times more active than NBPT. Therefore, in a commercial formulation, 2-NPT could be used at a concentration of 2.5% w/w, compared to 20% w/w for NBPT as per current standard practice.

Example 11

This example investigates the storage stability of formulations according to the invention. Concentrated solutions of urease inhibitors were stored at 40° C. for 8 weeks. At regular intervals, samples were withdrawn and the urease inhibitor content was analysed by HPLC. The results for the storage stability measured as concentration of NBPT as % w/w are shown in Table 4.

TABLE 4

| Solution | 0 weeks | 2 weeks | 6 weeks | 8 weeks |
|---|---|---|---|---|
| Agrotain ™ | 19.8 | 19.7 | 19.6 | 20.1 |
| Example 1 | 19.9 | 19.6 | 19.3 | 19.8 |
| Example 2 | 19.5 | 19.6 | 19.9 | 20.2 |

These results show that the concentrate liquids are stable at 40° C. for 8 weeks, with no change in the concentrations of NBPT, within experimental variance. These storage conditions are equivalent to about 12 months storage at ambient temperature.

Example 12

This example investigates the stability of urea granules treated with formulations according to the invention.

Methodology

Samples of coated urea were subjected to storage at 40° C. for 8 weeks. The results showing the concentration of NBPT as grams/kg of Urea are shown in Table 5. The concentrated inhibitor solutions (Agrotain™, Example 1 and Example 2) were applied to urea granules at the rate of 5 ml/kg of urea. The residual inhibitor present on the urea granules are shown in Table 5 as grams NBPT/kg of urea.

TABLE 5

| Solution | 0 weeks | 2 weeks | 6 weeks | 8 weeks |
|---|---|---|---|---|
| Agrotain ™ | 0.93 | 0.70 | 0.55 | 0.54 |
| Example 1 | 0.89 | 0.72 | 0.57 | 0.50 |
| Example 2 | 0.94 | 0.77 | 0.69 | 0.65 |

Based on the above results, the most stable formulation for coating onto urea granules was Example 2. After 8 weeks storage at 40° C., only about 35% of the urease inhibitor was lost from Example 2, while the other two formulations lost between 46 to 50% of the urease inhibitor.

A further experiment was conducted in which the urea samples were stored at 20° C. for 8 weeks. In that experiment, the urea granules lost only between 4 to 10% of the urease inhibitor. The best result was obtained with Example 2, which showed only 4% loss after 8 weeks storage at 20° C.

These results demonstrate the superior stability of Example 2 on the coated surface of urea granules. Based on the loss of only 35% of NBPT after 8 weeks storage at 40° C., the shelf life of treated urea will be at least 12 months under normal industrial storage conditions. The conventional treatment according to the prior art (Agrotain™), has a half life of 3 months.

Example 13

This example investigates the crush strength of urea granules treated with formulations according to the invention Urea granules of a uniform size having a substantially spherical shape are identified. The individual urea granules are placed between two plates and subjected to increasing pressure on a test plate until the granule fractures. The force required to cause the fracture is recorded with a force gauge (eg Digital Force Gauge DFE-050, Chatillon, Ametek). A mean of ten tests is recorded for each batch of urea.

The results for Mean Hardness (expressed as kg/granule) are shown in Table 6.

TABLE 6

| Sample | Fresh Sample | After 8 weeks at 20° C. | After 8 weeks at 40° C. |
| --- | --- | --- | --- |
| Agrotain ™ | 3.01 | 2.01 | 2.95 |
| Example 1 | 3.26 | 1.99 | 2.98 |
| Example 2 | 3.19 | 2.16 | 2.78 |
| Urea (untreated) | 3.21 | 2.28 | 3.02 |

These results show that the urea granules became softer after 8 weeks storage at 20° C., with a reduction in average crush strength from about 3.2 to 2.15 kg/granule. However, at 40° C. storage there was little change in the crush strength after 8 weeks, with the mean value falling to 3.0 kg/granule.

These results indicate that the urea granules coated with Examples 1 and 2 do not significantly lose mechanical strength compared to the untreated control. This property is important in large scale storage of treated urea in storage bins or hoppers, where formation of urea dust is deleterious to human health.

Example 14

This example investigates the water absorption of urea granules treated with formulations according to the invention. The storage experiment was conducted at 30° C., under either 70% or 75% humidity.

The water absorption was measured as the Critical Relative Humidity (CRH) being the % weight gain after 3 hours storage at each of Relative Humidity 70% and 75%. The urea granules were treated with the inhibitor solutions at the rate of 5 ml per kg of urea.

TABLE 7

| Sample | CRH at 70%/30° C. | CRH at 75%/30° C. |
| --- | --- | --- |
| Urea control | 0.3 | 1.8 |
| Agrotain ™ fresh | 0.7 | 2.3 |
| Agrotain ™ stored for 8 weeks at ambient | 0.3 | 2.3 |
| Agrotain ™ stored for 8 weeks at 40° C. | 0.3 | 1.8 |
| Example 1 fresh | 0.6 | 2.3 |
| Example 1 stored for 8 weeks at ambient | 0.6 | 2.0 |
| Example 1 stored for 8 weeks at 40° C. | 0.2 | 1.8 |
| Example 2 fresh | 0.6 | 2.5 |
| Example 2 stored for 8 weeks at ambient | 0.4 | 1.8 |
| Example 2 stored for 8 weeks at 40° C. | 0.4 | 2.8 |

These results show that all the treated urea granules (Agrotain™, Examples 1 and 2) perform similarly with respect to moisture absorption from the air at 70% and 75% humidity. While these results are higher than the untreated urea control, they are still acceptable under normal industrial storage conditions. Excessive moisture absorption will cause the urea granules to become soft and sticky and therefore difficult to transport and handle on a large scale.

Example 15

This example investigates the urease inhibition properties of urea granules treated with formulations according to the invention stored at 40° C.

Methodology

Urease Inhibition tests were performed using the method based on ammonium ion formation ($NH_4+$) in soil solution from the hydrolysis of urea as described in Example 9. The following samples were tested:

Urea coated with Agrotain™ (1.0 gram NBPT active/kg urea);

Urea coated with Example 1 (1.0 gram NBPT active/kg urea); and

Urea coated with Example 2 (1.0 gram NBPT active/kg urea).

Each of the above samples were tested on freshly prepared samples and on samples stored at 20° C. and 40° C. for 8 weeks. The same experimental conditions were used as in Example 9. The results for ammonium concentrations in soil solutions and % Inhibition after 20 days incubation are given in Table 8.

TABLE 8

| Test Solution | $NH_4^+$ (mg/l) | % Inhibition (20 days) |
| --- | --- | --- |
| Control Urea (no inhibitor) | 35.2 | |
| Urea + Agrotain ™-fresh sample | 8.2 | 77 |
| Urea + Agrotain ™-stored at 20° C. for 8 weeks | 9.7 | 72 |
| Urea + Agrotain ™-stored at 40° C. for 8 weeks | 7.9 | 78 |
| Urea + Example 1-fresh sample | 6.5 | 82 |
| Urea + Example 1-stored at 20° C. for 8 weeks | 6.6 | 81 |
| Urea + Example 1-stored at 40° C. for 8 weeks | 7.6 | 78 |
| Urea + Example 2-fresh sample | 6.2 | 82 |
| Urea + Example 2-stored at 20° C. for 8 weeks | 6.4 | 82 |
| Urea + Example 2-stored at 40° C. for 8 weeks | 6.7 | 81 |

These results show that the freshly prepared sample of Example 1 gave 82% inhibition of urea hydrolysis during 20 days incubation at 21° C. By comparison, the samples stored at 20° C. and 40° C. gave 81% and 78% inhibition, respectively. This indicates that the inhibitor NBPT was still stable and active after this storage period.

Similarly, Example 2 gave 82, 82 and 81% inhibition for the fresh sample and the samples stored at 20° and 40° C., respectively. These stability tests compare favorably with the results obtained with Agrotain™, which gave inhibition results of 77, 72 and 78% respectively (Table 8).

Example 16

This example investigates the efficacy of urea granules treated with formulations according to the invention.

Methodology

Replicated field tests in a random block design were performed in order to measure improvements in dry matter production, N-Uptake and N-Uptake Efficiency in winter rye grass, fertilised with control urea and urea treated with formulations according to the invention.

The urea application rates were 100 kg/Ha, equivalent to 46 kg Nitrogen/Ha. The urea granules were coated with 2, 3 or 5 ml of Example 1 per kg of urea. Agrotain™ was used at the rate of 5 ml per kg of Urea.

The results from one trial are shown in Table 9.

TABLE 9

| Fertiliser Added (Inhibitor ml/kg Urea) | Dry Matter Kg/Ha | N-Uptake KWH | N-Uptake % Efficiency |
|---|---|---|---|
| Nil (Blank) | 1525 | 45.5 | 0 |
| Urea (Control) | 2062 | 68.1 | 49.1 |
| Urea + 5 ml Example 1 | 2546 | 87.7 | 91.7 |
| Urea + 3 ml Example 1 | 2411 | 81.8 | 78.8 |
| Urea + 2 ml Example 1 | 2561 | 81.5 | 78.3 |
| Urea + 5 ml Agrotain ™ | 2301 | 74.8 | 63.7 |
| LSD (P = 0.05) | 431 | 17.3 | |
| CV % | | 14.1 | 17.8 |

Based on the above results, the Example 1 treatments applied at 2 or 5 ml were significantly more effective in producing ryegrass dry matter than the urea control. The Example 1 treatments did not deliver statistically significant improvements in the Dry Matter yield and N-Uptake over the Agrotain™ treated urea. There is however a trend which favours the Example 1 treatments (even at lower rates of addition to the urea). N-Uptake % Efficiency of approximately 80-90% was achieved with Example 1 treatments, which compares favourably with the approximately 50% efficiency with untreated Urea. The conventional treatment with Agrotain™ gave about 60% efficiency.

N-Uptake Efficiency=(Sample Uptake−Blank Uptake)*100/46

These results show that urea treated with the formulation according to the invention had a superior N-Uptake % Efficiency compared to the conventional treatment with Agrotain™.

Example 17

This example investigates the stability of the urease inhibitor formulation according to the invention when coated onto urea granules.

An industrial scale production was carried out on 15 Tonnes of urea, which was treated either with the standard inhibitor formulation Agrotain™ or with the urease inhibitor formulation according to the invention as described in Example 3.

The liquid product Agrotain™ was applied at the rate of 3 liters per Tonne of urea; whereas the liquid inhibitor of Example 3 was applied at the lower rate of 2 liters per Tonne.

These two batches of treated urea were stored at ambient temperature and humidity for a period of 8 weeks from 17 Mar. 2011 at Charles Sturt University, Wagga Wagga, NSW, Australia.

Stability tests were performed on samples stored under the following conditions:

Bulk Urea—fourteen (14) Tonnes were placed in a dry area of the manufacturing plant on a concrete floor in a large pile One Tonne Bag—the treated Urea was also stored in a one Tonne "bulk-bag" typically used for storage and transport of bulk Urea 25 Kg Bag—the treated Urea was stored in a standard 25 Kg woven plastic bag typically used for storage of dry fertilisers.

The residual active constituent NBPT was analysed by HPLC on each of the samples at regular intervals, as shown in Table 10.

TABLE 10

Residual NBPT (% w/w) on Treated Urea after Storage

| | Agrotain | | | Example 3 | | |
|---|---|---|---|---|---|---|
| Storage Period weeks | 25 Kg Bags | One Tonne Bags | Bulk Urea | 25 Kg Bags | One Tonne Bags | Bulk Urea |
| 0 | 0.062 | 0.062 | 0.062 | 0.038 | 0.038 | 0.038 |
| 2 | | | 0.055 | | | 0.038 |
| 4 | 0.015 | 0.026 | 0.047 | 0.034 | 0.033 | 0.039 |
| 6 | | | 0.039 | | | 0.041 |
| 8 | 0.016 | 0.025 | 0.049 | 0.029 | 0.035 | 0.042 |
| % Loss after 8 weeks | 74 | 60 | 21 | 20 | 3 | 0 |

These results show the superior stability of NBPT when applied to urea using a urease inhibitor formulation according to the invention. After 8 weeks storage, the Bulk Urea still showed 0.042%+0.02% as NBPT, compared with the original value of 0.038%+0.02%. This demonstrates that there was no loss of active NBPT in the Bulk Urea after 8 weeks storage when a urease inhibitor formulation according to the invention was used.

In contrast, the urea treated with Agrotain™ had lost 21% of the applied NBPT in the Bulk Urea sample, falling from the original value of 0.062% to a reduced level of 0.049% after 8 weeks storage.

In the case of the One Tonne Bags, the urea treated with the Example 3 formulation according to the invention still retained 0.035% as NBPT (a loss of only 3% after 8 weeks); whereas the Agrotain™-treated urea contained only 0.025% as NBPT (a loss of 60% after 8 weeks).

The losses in the 25 Kg bags were even higher. The Agrotain™-treated urea lost 74% of the applied NBPT; whereas the urea treated with the Example 3 formulation according to the invention lost only 20% of the active constituent.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

The claims defining the invention are as follows:

1. A liquid urease inhibitor formulation for application to urea-based fertilizers and waste containing urea compounds comprising:

(a) a urease inhibitor selected from the group consisting of N-substituted thiophosphoric triamides and N-substituted phosphoric triamides represented by Structure I and mixtures thereof,

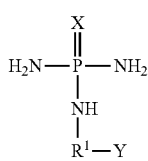

Structure I wherein X=O or S, $R^1$=unsubstituted and substituted $C_4$-$C_6$ alkyl, unsubstituted and substituted $C_5$-$C_8$ cyclo alkyl, phenyl and substituted phenyl having a nitro, amino, alkyl, or halide substituent; and Y=H, $NO_2$, halide, $NH_2$ or $C_1$ to $C_8$ alkyl; and (b) a primary solvent selected from the group consisting of dialkyl sulfones according to Structure II, polymethylene cyclic sulfones according to Structure III, and mixtures thereof;

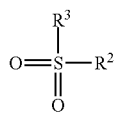

Structure II wherein $R^2$ = alkyl $C_1$ to $C_6$
$R^3$ = alkyl $C_1$ to $C_6$

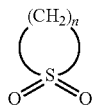

Structure III wherein $n$ = 3 to 6 wherein the urease inhibitor is soluble in the primary solvent.

2. The liquid urease inhibitor formulation according to claim 1 further comprising:

(c) a buffering agent and stabilizer selected from the group consisting of hydroxyethyl and hydroxypropyl amines according to Structure IV, in which the amine can be a primary, secondary or tertiary amine and the number of hydroxyethyl or hydroxypropyl groups can be 1, 2 or 3,

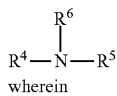

Structure IV wherein $R^4$ and $R^5$ are independently H, $C_1$-$C_6$ alkyl or

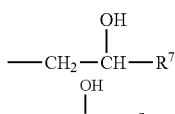

$R^7$ = H or $CH_3$.

3. The liquid urease inhibitor of claim 1 further comprising:

(d) a non-ionic surfactant having wetting agent properties selected from the group consisting of aliphatic alcohol alkoxylates, alkylphenol alkoxylates and mixtures thereof.

4. The liquid urease inhibitor formulation of claim 1 wherein the amount of the urease inhibitor is in the range from 0.5 to 51% by weight of the total formulation.

5. The liquid urease inhibitor formulation of claim 1 wherein the amount of primary solvent is in the range from 10 to 80% by weight of the total formulation.

6. The liquid urease inhibitor formulation of claim 2 wherein the amount of buffering agent and stabilizer is in the range from 1 to 50% by weight of the total formulation.

7. The liquid urease inhibitor formulation of claim 3 wherein the amount of the nonionic surfactant is in the range from 0.1 to 2.0% by weight of the total formulation.

8. The liquid urease inhibitor formulation of claim 1 for application to urea-based fertilizers and waste containing urea compounds wherein the primary solvent is tetramethylene sulfone.

9. The liquid urease inhibitor formulation of claim 2 wherein the buffering agent and stabilizer is selected from the group consisting of triethanolamine, monoethanolamine and mixtures thereof.

10. The liquid urease inhibitor formulation of claim 1 wherein the urease inhibitor is selected from the group consisting of N-butyl thiophosphoric triamide, 2-nitrophenyl phosphoric triamide, N-cyclohexyl phosphoric triamide and mixtures thereof.

11. A method for inhibiting the urease hydrolysis of urea-containing fertilizer, soil or waste containing urea compounds, the method comprising the step of applying a liquid urease inhibitor formulation to the urea-containing fertilizer, soil or waste containing urea compounds, the liquid urease inhibitor formulation comprising:

(a) a urease inhibitor selected from the group consisting of N-substituted thiophosphoric triamides and N-substituted phosphoric triamides represented by Structure I and mixtures thereof,

Structure I wherein X=O or S, $R^1$=unsubstituted and substituted $C_3$-$C_6$ alkyl, unsubstituted and substituted $C_5$-$C_8$ cyclo alkyl, phenyl and substituted phenyl having a nitro, amino, alkyl, or halide substituent; and Y=H, $NO_2$, halide, $NH_2$ or $C_1$ to $C_8$ alkyl; and (b) a primary solvent selected from the group consisting of dialkyl sulfones according to Structure II, polymethylene cyclic sulfones according to Structure III, and mixtures thereof;

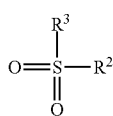

wherein $R^2$ = alkyl $C_1$ to $C_6$
$R^3$ = alkyl $C_1$ to $C_6$

Structure II

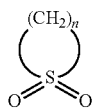

wherein $n$ = 3 to 6

Structure III wherein the urease inhibitor is soluble in the primary solvent.

12. The method of claim 11 wherein the urea-containing fertilizer is urea granules and the step of applying the liquid urease inhibitor formulation comprises spraying the formulation onto the surface of the urea granules, or melting the urea granules with the formulation to form a solid mixture.

13. The method of claim 11 wherein the inhibition of urease hydrolysis of urea in soil is for at least 14 days.

14. The method of claim 11, wherein the liquid urease inhibitor formulation further comprises:
(c) a buffering agent and stabilizer selected from the group consisting of hydroxyethyl and hydroxypropyl amines according to Structure IV, in which the amine can be a primary, secondary or tertiary amine and the number of hydroxyethyl or hydroxypropyl groups can be 1, 2 or 3,

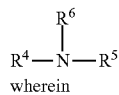

Structure IV wherein $R^4$ and $R^5$ are independently H, $C_1$-$C_6$ alkyl or

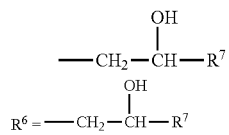

$R^7$ = H or $CH_3$.

15. The method of claim 11 further comprising:
(d) a non-ionic surfactant having wetting agent properties selected from the group consisting of aliphatic alcohol alkoxylates, alkylphenol alkoxylates and mixtures thereof.

16. The method of claim 11, wherein the amount of the urease inhibitor is in the range from 0.5 to 51% by weight of the total formulation.

17. The method of claim 11, wherein the amount of primary solvent is in the range from 10 to 80% by weight of the total formulation.

18. The method of 17, wherein the amount of buffering agent and stabilizer is in the range from 1 to 50% by weight of the total formulation.

19. The method of claim 15, wherein the amount of the nonionic surfactant is in the range from 0.1 to 2.0% by weight of the total formulation.

20. The method of claim 11, wherein the primary solvent is tetramethylene sulfone.

21. The method of claim 14, wherein the buffering agent and stabilizer is selected from the group consisting of triethanolamine, monoethanolamine and mixtures thereof.

22. The method of claim 11, wherein the urease inhibitor is selected from the group consisting of N-butyl thiophosphoric triamide, 2-nitrophenyl phosphoric triamide, N-cyclohexyl phosphoric triamide and mixtures thereof.

23. A liquid urease inhibitor formulation for application to urea-based fertilizers and waste containing urea compounds comprising:
(a) a urease inhibitor selected from the group consisting of N-substituted thiophosphoric triamides and N-substituted phosphoric triamides represented by Structure I and mixtures thereof,

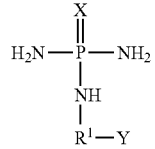

Structure I wherein X=O or S, $R^1$=unsubstituted and substituted $C_3$-$C_6$ alkyl, unsubstituted and substituted $C_5$-$C_8$ cyclo alkyl, phenyl and substituted phenyl having a nitro, amino, alkyl, or halide substituent; and Y=H, $NO_2$, halide, $NH_2$ or $C_1$ to $C_8$ alkyl;

(b) a primary solvent selected from the group consisting of dialkyl sulfones according to Structure II, polymethylene cyclic sulfones according to Structure III, and mixtures thereof;

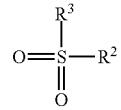

Structure II wherein $R^2$ = alkyl $C_1$ to $C_6$
$R^3$ = alkyl $C_1$ to $C_6$

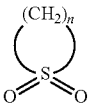

Structure III wherein $n$ = 3 to 6 wherein the urease inhibitor is soluble in the primary solvent; and (c) a buffering agent and stabilizer selected from the group consisting of hydroxyethyl and hydroxypropyl amines according to Structure IV, in which the amine can be a primary, secondary or tertiary amine and the number of hydroxyethyl or hydroxypropyl groups can be 1, 2 or 3,

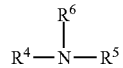

Structure IV wherein
$R^4$ and $R^5$ are independently H, $C_1$—$C_6$ alkyl or —$CH_2$—$\overset{OH}{CH}$—$R^7$

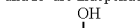

$R^7$ = H or $CH_3$.

* * * * *